(12) United States Patent
Ito

(10) Patent No.: US 9,028,693 B2
(45) Date of Patent: May 12, 2015

(54) APPARATUS FOR COUNTERCURRENT CHROMATOGRAPHY

(75) Inventor: Yoichiro Ito, Bethesda, MD (US)

(73) Assignee: The United States of America, as represented by the Secretary, Department of Health and Human Services, Washington, DC (US)

(*) Notice: Subject to any disclaimer, the term of this patent is extended or adjusted under 35 U.S.C. 154(b) by 866 days.

(21) Appl. No.: 12/746,436

(22) PCT Filed: Dec. 3, 2008

(86) PCT No.: PCT/US2008/085439
§ 371 (c)(1),
(2), (4) Date: Jun. 4, 2010

(87) PCT Pub. No.: WO2009/073746
PCT Pub. Date: Jun. 11, 2009

(65) Prior Publication Data
US 2010/0276351 A1    Nov. 4, 2010

Related U.S. Application Data

(60) Provisional application No. 61/012,354, filed on Dec. 7, 2007.

(51) Int. Cl.
*G01N 30/42*    (2006.01)
*B01D 15/18*    (2006.01)

(52) U.S. Cl.
CPC ............ *G01N 30/42* (2013.01); *B01D 15/1807* (2013.01); *B01D 15/18* (2013.01)

(58) Field of Classification Search
CPC ...... G01N 30/42; B01D 15/18; B01D 15/1807
USPC ........................................ 210/635, 657, 198.2
See application file for complete search history.

(56) References Cited

U.S. PATENT DOCUMENTS

| | | | | |
|---|---|---|---|---|
| 4,324,661 A * | 4/1982 | Ito | ................................. | 210/635 |
| 4,414,108 A * | 11/1983 | Ito | ............................. | 210/198.2 |
| 4,551,251 A * | 11/1985 | Kolobow et al. | .............. | 210/635 |
| 4,900,446 A * | 2/1990 | Anderson | ..................... | 210/657 |
| 4,968,428 A * | 11/1990 | Nunogaki | ..................... | 210/635 |
| 5,104,531 A * | 4/1992 | Ito et al. | ..................... | 210/198.2 |
| 5,217,608 A * | 6/1993 | Conway | ..................... | 210/198.2 |
| 6,379,973 B1 * | 4/2002 | Ito | ................................. | 436/178 |
| 6,537,452 B1 * | 3/2003 | de La Poype et al. | ..... | 210/198.2 |
| 6,913,692 B2 * | 7/2005 | Margraff et al. | .......... | 210/198.2 |
| 7,351,333 B2 * | 4/2008 | Hawes et al. | .............. | 210/198.2 |
| 7,815,799 B2 * | 10/2010 | Pfeiffer | ..................... | 210/198.2 |

FOREIGN PATENT DOCUMENTS

| | | | |
|---|---|---|---|
| JP | 59-79157 | * | 5/1984 |
| WO | WO 2004/085020 | * | 10/2004 |

OTHER PUBLICATIONS

Abstract of Japan Patent No. 59-79157 Undated.*
Ito "Improved Spiral Disk Assembly for High Speed Counter-Current Chromatography", Journal of Chromatography A 1017 (2003), pp. 71-81.*

* cited by examiner

*Primary Examiner* — Ernest G Therkorn
(74) *Attorney, Agent, or Firm* — Polsinelli PC; Patrick C. Woolley; Ari M. Bai

(57) ABSTRACT

A plate apparatus for use in countercurrent chromatography is disclosed which comprises a disk shaped tube support (60) having a tube support pattern form in an upper surface (63) of the support and configured to accommodate at least one layer of fluid flow tubing (70), wherein the pattern comprises at least one spiral groove (62) and at least one return path (72).

8 Claims, 5 Drawing Sheets

APPARATUS FOR COUNTERCURRENT CHROMATOGRAPHY

CROSS REFERENCE TO RELATED APPLICATIONS

This is the national stage of International Application No. PCT/US2008/085439, filed on Dec. 3, 2008, which claims the benefit of U.S. Provisional Patent Application No. 61/012,354, filed on Dec. 7, 2007, the contents of both of which are incorporated herein by reference.

BACKGROUND OF THE INVENTION

1. Field of the Invention

The invention relates to countercurrent chromatography systems, and more particularly to an improved instrument design for use in countercurrent chromatography.

2. Description of the Related Art

Chromatography is a separation process that is achieved by distributing the substances to be separated between a mobile phase and a stationary phase. Those substances distributed preferentially in the moving phase pass through the chromatographic system faster than those that are distributed preferentially in the stationary phase. As a consequence, the substances are eluted from the column in inverse order of their distribution coefficients with respect to the stationary phase.

Chromatography is widely used for the separation, identification, and determination of the chemical components in a complex mixture. Chromatographic separation can be utilized to separate gases, volatile substances, nonvolatile material, polymeric material, and a wide variety of organic and biological substances.

The performance of countercurrent chromatography systems depends largely on the amount of stationary phase retained in the column, which determines both the resolving power of the solute peaks and the sample loading capacity. Numerous countercurrent chromatography systems have been developed to optimize the retention of the stationary phase of a sample in the column. The maximum attainable retention level tends to fall sharply with the application of higher flow rates of the mobile phase, resulting in loss of peak resolution. Consequently, the applicable flow rate has become one of the major limiting factors in countercurrent chromatography.

Some countercurrent chromatography systems utilize a complex hydrodynamic motion in two solvent phases within a column comprising a rotating coiled tube. If, for example, a horizontally mounted coil is filled with water and is rotated around its own axis, any object, either heavier or lighter than the water present in the column will tend to move toward one end of the coil. This end is then called the "head" and the other end, the "tail" of the coil.

When the coil is filled with two immiscible solvent phases, the rotation establishes a hydrodynamic equilibrium between the two solvent phases, where the two phases are distributed in each turn at a given volume ratio (equilibrium volume ratio) and any excess of either phase remains at the respective tail of the coil for each solvent.

When the coil is filled with one of the solvents as a stationary phase and the other solvent is eluted from the coil from its head end, the hydrodynamic equilibrium tends to maintain the original equilibrium volume ratio of the two phases in the coil and thereby a certain volume of the stationary phase is permanently retained in the coil while the two phases are undergoing vigorous agitation with rotation of the coil. As a result, the sample solutes present in one phase and introduced locally at the inlet of the coil are subjected to an efficient partition process between the two phases and are chromatographically separated according to their partition coefficients.

In some cases, countercurrent chromatography utilizes a multi-layer coil as a separation column to produce a high efficiency separation with relatively favorable retention of the stationary phase in many solvent systems. Thus, countercurrent chromatography has been employed to achieve efficient separation of compounds in a sample solution under relatively high flow rates.

A structure that can be used in a countercurrent chromatography column assembly comprises a plurality of separation disks having a plurality of spiral flow channels carved, etched, or molded on the surface of a first side of each separation disk as described in U.S. Pat. No. 6,379,973, for example. The spiral flow channel has an inlet end and an outlet end, wherein fluid typically flows along the path of the spiral channel from the inlet end to the outlet end. The spiral channel of one separation disk can be serially connected to the spiral channel of another separation disk by stacking multiple separation disks adjacent to one another with a septum separating each pair. Preferably, an outlet end of a channel on one disk connects to the inlet end of the channel on the next adjacent disk.

An alternative structure that can be used in a countercurrent chromatography column assembly is described in international Patent Publication WO/2004/085020, wherein the column is formed as a length of tubing which is installed within one or more grooves in a plate or disk (also referred to herein as a tube support).

One embodiment of such a plate or disk shaped tube support for use in a countercurrent chromatography apparatus is illustrated in FIGS. 1 and 2. FIG. 1A is a top view, showing the upper surface, of the tube support. FIG. 1B is a cross-sectional view of the tube support taken along the line B-B of FIG. 1A. FIG. 1C shows the lower surface of the tube support.

In this embodiment, four spiral grooves 22, 24, 26, 28 are etched into the upper surface of the tube support. Additionally, four return paths 32, 34, 36, 38 are etched into the lower surface of the tube support. Notches 42, 44, 46, 48 are etched into the tube support proximate to locations $O_1$, $O_2$, $O_3$, and $O_4$, to allow for tubing to wrap around the tube support from the upper surface to the lower surface. Similarly, notches 52, 54, 56, 58 are etched into the tube support proximate to locations $I_1$, $I_2$, $I_3$, and $I_4$ to allow for tubing to wrap around the tube support from the lower surface to the upper surface.

In operation, tubing 50 is placed within the grooves of the tube support, winding on the upper surface from $I_1$ to $O_1$, then returning via a return path on the lower surface of the tube support from $O_1$ to $I_2$. FIG. 2 shows the cross-sectional view of the tube support of FIG. 1, with tubing in place.

As vertical portions of tubing 55 do nothing to contribute to countercurrent chromatography, the length of tubing winding between the upper surface and lower surface via the notches is wasted. Additionally, as many layers of tubing are placed within the tube support, the notches may soon fill with tubing, limiting the number of spirals of tubing which can be placed in the tube support. Furthermore, the requirement to etch a pattern on both sides of the disk or plate, and the necessity of the notches, increases the cost of manufacturing.

SUMMARY OF THE INVENTION

In one aspect of the invention, a tube support for use in a countercurrent chromatography apparatus comprises first and second opposed surfaces, a plurality of interleaved spiral grooves forming a continuous channel in the first surface and configured to accommodate at least one layer of fluid flow tubing, wherein the spiral grooves have an inlet space and an outlet space, at least one radial slot also formed in the first surface connecting the inlet space of one spiral groove with the outlet space of another spiral groove, and at least one entry point positioned on the second surface to thread fluid flow tubing into at least one inlet space.

In another aspect of the invention, a disk shaped tube support for use in a countercurrent chromatography apparatus comprises an upper surface and a tube support pattern formed in the upper surface and configured to accommodate at least one layer of fluid flow tubing, wherein the pattern comprises at least one spiral groove and at least one return path.

Another aspect of the invention is a countercurrent chromatography apparatus comprising a disk having a tube support pattern formed in an upper surface of the disk and at least one layer of fluid flow tubing positioned in the tube support pattern, wherein the pattern comprises at least one spiral groove and at least one return path.

An additional aspect of the invention is a method of manufacturing a plate assembly for use in high speed countercurrent chromatography comprising forming a forming a tube support pattern in an upper surface of a plate, wherein the tube support pattern comprises at least one spiral groove and at least one return path.

DETAILED DESCRIPTION OF THE PREFERRED EMBODIMENT

Embodiments of the invention will now be described with reference to the accompanying Figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore embodiments of the invention may include several novel features, no single one of which is solely responsible for its desirable attributes or which is essential to practicing the inventions herein described.

Although embodiments of the invention have various applications, many advantageous embodiments of the present invention are directed to an improved plate apparatus for use in countercurrent chromatography. Applicable chromatography techniques include those using synchronous planetary motion such as X-type, J-type, and I-type chromatography. The apparatus and methods described herein are especially advantageous when applied to high-speed countercurrent chromatography (HSCCC) with high flow rates.

The plate design may also be employed in large column applications for industrial-scale separations of samples by mounting the column assembly on a slowly rotating horizontal shaft.

Some aspects of the invention are based, in part, on the fact that system cost and performance is improved when the column used in counter current chromatography is formed as a length of tubing which is installed within one or more grooves in a plate or disk (also referred to herein as a tube support).

Figure 3A:
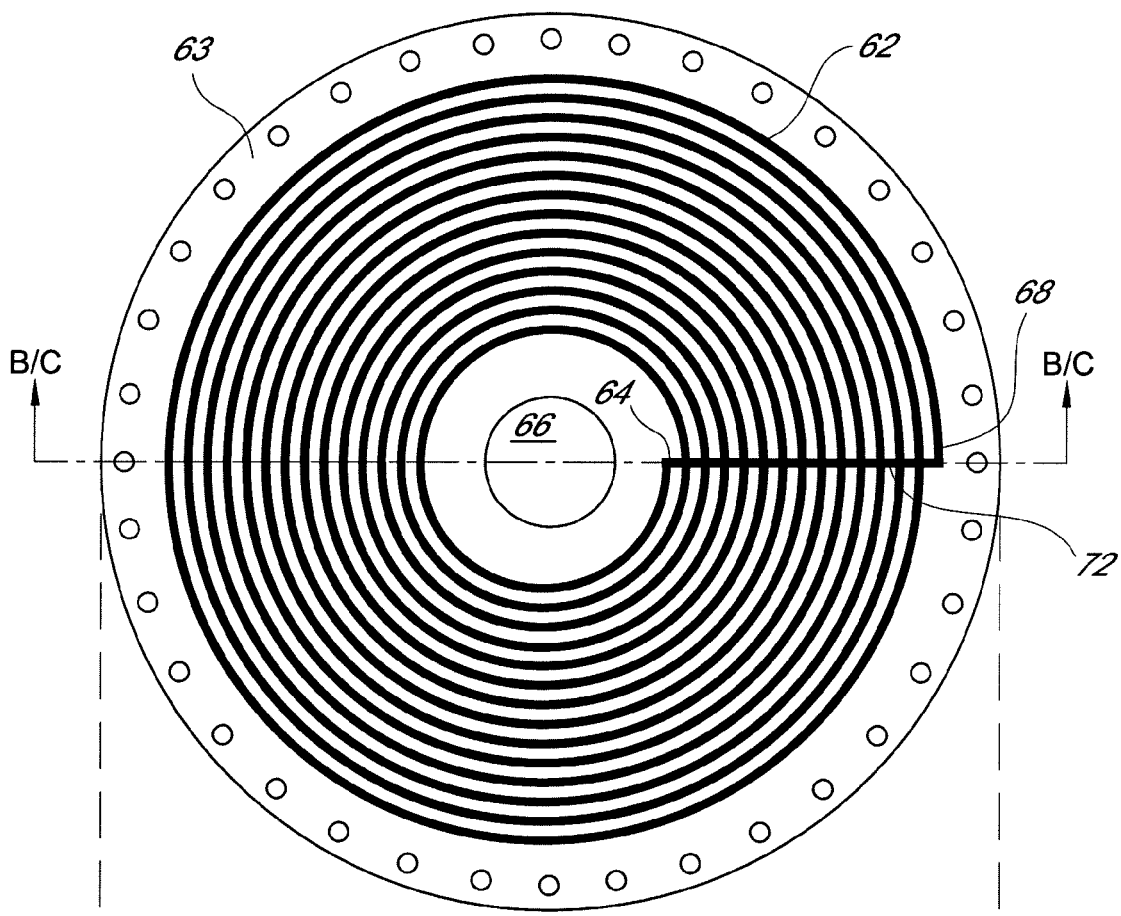
FIG. 3A is a top view of a tube support for use in high speed countercurrent chromatography.
Figure 3B:
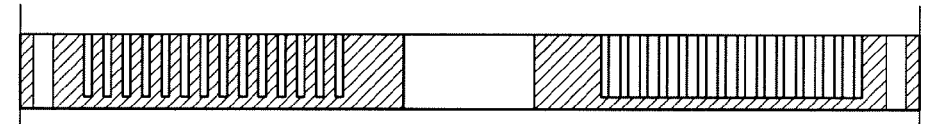
FIG. 3B is a cross-sectional view of the tube support of FIG. 3A taken along line B-B.

One embodiment of a plate or disk shaped tube support 60 for use in a countercurrent chromatography apparatus is illustrated in FIGS. 3A and 3B. FIG. 3A is a top view of the tube support 60. FIG. 3B is a cross-sectional view of the tube support 60 taken along line A-A of FIG. 3A.

The tube support 60 comprises a single spiral groove 62 carved, etched, or molded in an upper surface 63 of the tube support 60 and configured to accommodate or support a length of fluid flow tubing, as described further below. Although the spiral groove 62 is illustrated as having a rectangular cross-section, it will be appreciated that grooves having different geometrically shaped cross-sections may be used, such as a groove with an arcuate or semicircular cross-section.

The spiral groove 62 originates at an inner end 64 located proximal to a center opening 66 of the tube support 60, and ends at an outer end 68 proximal to an outer rim 70 of the tube support 60. In this embodiment, the inner end 64 and outer end 68 are located at substantially the same angular position on the tube support 60. A length of tubing having an outer diameter approximately equal to or smaller than the width of the groove can then be positioned in the spiral groove 62 with a first end at the inner end 64 and a second end at the outer end 68 to provide a fluid flow path. The tubing can comprise a flexible fluid flow tubing material, a variety of which are well known in the art and are widely commercially available. In one advantageous embodiment, the tubing comprises polytetrafluoroethylene (PTFE). Other polymers may also be used such as polyfluorinated ethylene propylene copolymer (FEP). The tube support 60 itself can be formed from a number of materials, including metal or plastic. For example, the tube support 60 may comprise aluminum, nylon, foam plastic, polyethylene, or polypropylene.

Figures 1A, 1B:
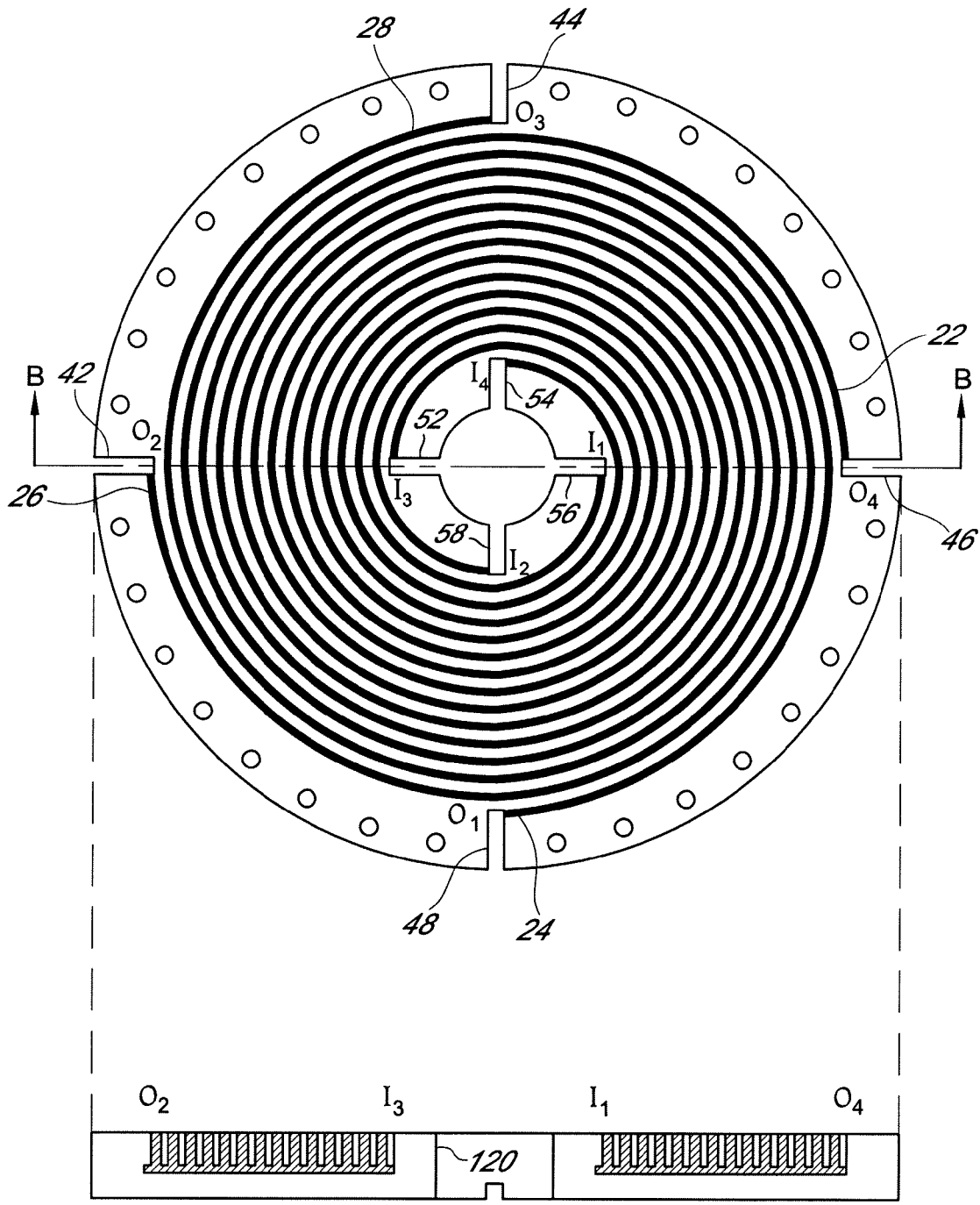
FIG. 1A is a top view, showing the upper surface, of a prior art tube support.
FIG. 1B is a cross-sectional view of the tube support of FIG. 1A taken along the line B-B.
Figure 1C:
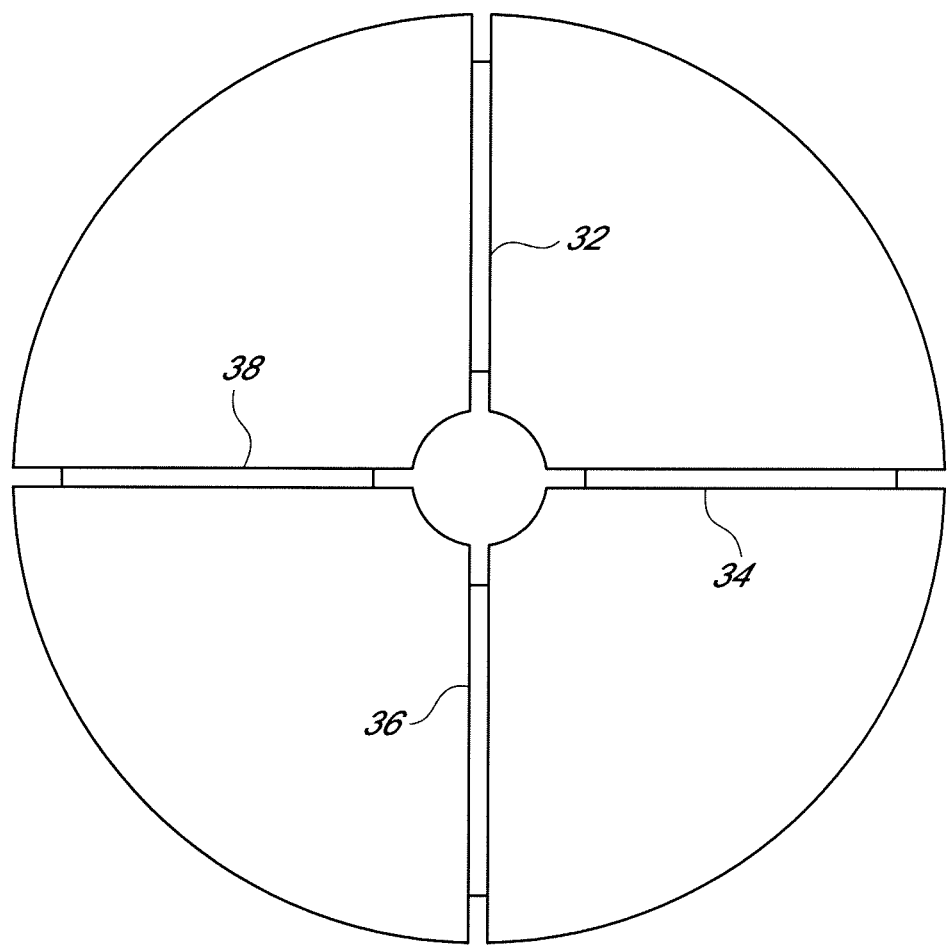
FIG. 1C shows the lower surface of the tube support of FIG. 1A.
Figure 2:
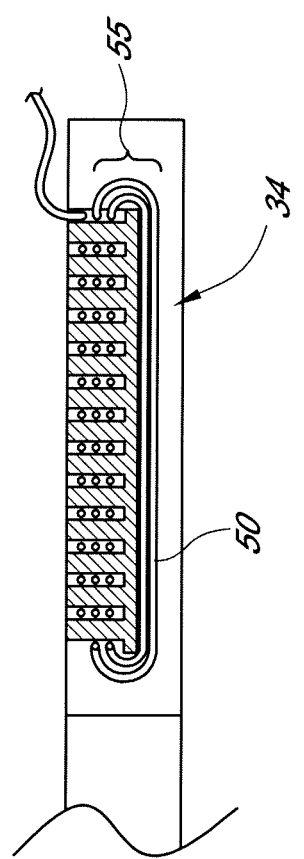
FIG. 2 shows the cross-sectional view of the tube support of FIG. 1, with tubing in place.

To facilitate accommodation of multiple layers of tubing, a return path 72 is provided in the tube support 60 for the tubing between the outer end 68 and inner end 64 of the spiral groove 62. In contrast with prior art tube support of FIGS. 1 and 2, the return path is carved, etched, or molded in the upper surface 63 in the same manner as the spiral groove 62. By placing the return path 72 on the same surface as the spiral groove 62, the amount of tubing in a vertical position is minimized, increasing the efficiency of the countercurrent chromatography apparatus. Additionally, this has the advantage of only requiring machining of the disk on one surface and removes the need to have notches machine into the tube support 60. Both of these advantages decrease the cost of manufacturing.

Figure 3C:
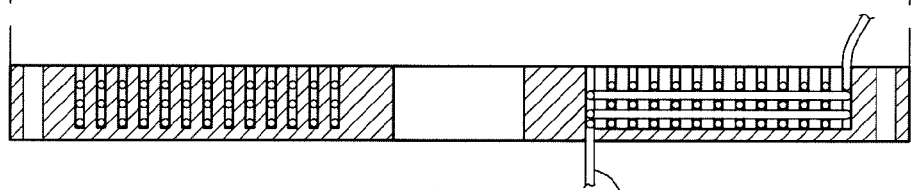
FIG. 3C is a cross-sectional view of the tube support of FIG. 3A, with tubing in place.

FIG. 3C is a cross-sectional view of the tube support of FIG. 3A, with tubing in place. In an exemplary operation, a section of tubing 70 is threaded into an entry point in the bottom of the plate so as to be placed in the inlet space 64 of the spiral groove 62 and laid around the spiral in the groove to the outlet space 68 of the spiral groove 62. The tubing is then placed in the return path 72, laying over the tubing previously placed at the bottom of the spiral groove 62 and back to the inlet space 64. The tubing is then placed again in the spiral groove 62, on top of previously laid tubing, such that two openings are again on separate ends. This process may be repeated.

It will be appreciated by a person skilled in the art that the return path 72 is not restricted to radial or groove configuration, and other positions are possible so long as the extent of the tubing in the return path is less than in the proximate spiral groove so as to reduce dead space. Although generally not optimal, using a return path having a first end and a second end at different angular positions is possible.

The embodiment of the tube support 60 with a single return path 72 described above provides an asymmetrical distribution of the tubing and groove, which may require careful balancing of the column for centrifugation. Additionally, with only a single return path 72, tubing builds up at the intersection of the return path 72 and the spiral groove 62 when many layers of tubing are used.

In one embodiment, multiple interleaved spiral grooves are formed symmetrically around the center of a plate or disk shaped tube support for use in a countercurrent chromatography apparatus, such that the spiral pitch is increased as compared to the spiral pitch of the single spiral groove embodiment of FIG. 3.

Figures 4A, 4B:
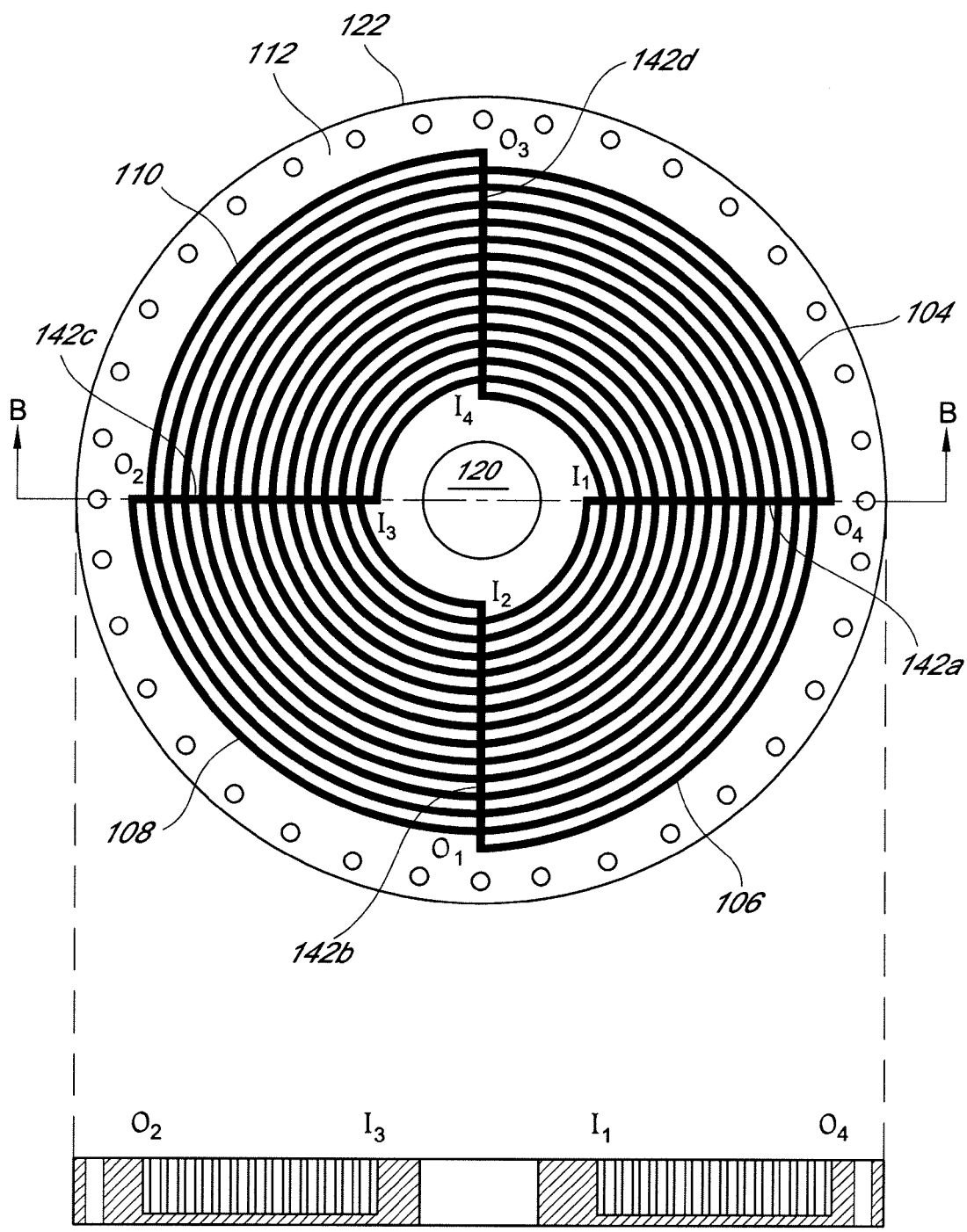
FIGS. 4A and 4B are a top plan view and cross section of a tube support with a plurality of interleaved spiral grooves and a plurality of return paths.

FIG. 4 is a top plan view of a tube support 100 having a plurality of interleaved spiral grooves and a plurality of return paths. The tube support 100 comprises four interleaved spiral grooves 104, 106, 108, and 110 formed in an upper surface 112 of the tube support 100. It will be appreciated, however, that the number of spiral grooves can vary, and the number of grooves illustrated and described herein is only exemplary in nature. Each spiral groove 104, 106, 108, 110 has an inner end denoted $I_1$, $I_2$, $I_3$, and $I_4$, respectively, located proximal to a center opening 120 of the tube support 100.

Each groove 104, 106, 108, 110 spirals from its inner end $I_1$, $I_2$, $I_3$, and $I_4$ to an outer end denoted $O_1$, $O_2$, $O_3$, and $O_4$, respectively, located proximal to an outer rim 122 of the tube support 100. As discussed above with respect to the single spiral embodiment, the interleaved spiral grooves 104, 106, 108, 110 can have a cross-section other than the rectangular shape illustrated, such as an arcuate or semi-circular shape.

In the embodiment of the tube support 100 illustrated in FIG. 4, the inner ends $I_1$, $I_2$, $I_3$, and $I_4$ are positioned along an inner circumference of the tube support 100 at 90° intervals, and each spiral groove 104, 106, 108, and 110 forms 3.25 spiral turns such that the outer end ($O_1$, $O_2$, $O_3$, and $O_4$) of a given groove is located at substantially the same angular position as the inner end ($I_2$, $I_3$, $I_4$ and $I_1$) of the next groove. Thus, $O_1$ is at the same angular orientation as $I_2$, $O_2$ is at the same angular orientation as $I_3$, etc.

Four return paths 142a, 142b, 142c, 142d are provided between the outer end and complementary inner end. As previously discussed, it will be appreciated by a person skilled in the art that the return path is not restricted to a radial or groove configuration, and other return path configurations are anticipated. Tubing can be positioned on the tube support 100 in a procedure similar to that previously described with respect to the tube support 60 having a single spiral groove.

More specifically, a length is tubing is laid along the first spiral groove 104 starting at point $I_1$ and finishing at point $O_1$. The tubing is then laid along the return path 142a between points $O_1$ and $I_2$. The tubing is then laid between points $I_2$ and $O_2$ along spiral groove 106. The process continues to points $I_3$, $O_3$, $I_4$, and $O_4$. Tubing may be laid along the return path 142d between points $O_4$ and $I_1$ and the process can repeat.

Tubing with a circular cross section can be used to provide a fluid flow path on the tube support along the spiral and radial grooves, however, tubing having a cross-section with a non-circular geometry or convoluted shape can provide improved results. For example, tubing with a circular cross section has been found to produce a plug flow in tubing with a small diameter, particularly for the organic mobile phase of a two-phase solvent system with high interfacial tension and/or small density differences between the two phases.

Such an effect may be largely reduced by using tubing with a rectangular or triangular cross section. In addition, tubing having a cross section with a rectangular or triangular cross section, for example, can provide improved stacking conditions for implementing multiple levels of spiral fluid flow paths on a single tube support. Alternately, tubing having a non-circular cross section can be twisted before positioning on the tube support so as to improve the partition efficiency.

Any of the above embodiments may also be configured with a tubing entry point. Such an entry point may be hole extending through the entirety of the tube support to allow tubing to be threaded through prior to being laid in the groove of the tube support. The entry point may be, for example, at point $I_1$ of FIG. 3 or FIG. 4, or, indeed, at any labeled point or elsewhere along the groove.

Although two embodiments of the tube support pattern were described, namely a single spiral with a single return path and a plurality of interleaved spirals with a plurality of return paths, other embodiments may be possible or advantageous in use. For example, the pattern formed in the upper surface of the tube support may be a single spiral with a plurality of return paths. This embodiment maintains the spiral pitch of the tube support of FIG. 3, but is more balanced as in the tube support of FIG. 4. In another embodiment, the tube support pattern comprises the superposition of two spirals with different pitches both etched into the upper surface, and an appropriate return path. Because the fluid is maintained in the tube, this tube support can be used with either etched spiral or both depending upon how the tubing is laid. The walls of the tube support need not necessarily be solid or continuous, and may be at least partially formed from wall segments or even comprise a multitude of "pins" on the tube support. Although spirals with a constant spiral pitch have been described, some embodiments may include tubing support patterns having a spiral pitch that varies throughout the spiral. To couple two disks with a continuous length of tubing, a slit can be provided in the periphery of the disk, aligned with the final outlet space. The tube can then be routed to the upper surface of the next disk, then along a return path to the first inlet space.

The foregoing description sets forth various preferred embodiments and other exemplary but non-limiting embodiments of the inventions disclosed herein. The description gives some details regarding combinations and modes of the disclosed inventions. Other variations, combinations, modifications, modes, and/or applications of the disclosed features and aspects of the embodiments are also within the scope of this disclosure, including those that become apparent to those of skill in the art upon reading this specification. Thus, the scope of the inventions claimed herein should be determined only by a fair reading of the claims that follow.

What is claimed is:

1. A tube support for use in a countercurrent chromatography apparatus, comprising:
   first and second opposed surfaces;
   a plurality of interleaved spiral grooves forming a continuous channel in the first surface and configured to accommodate at least one layer of fluid flow tubing, wherein the spiral grooves have an inlet space and an outlet space formed on the first surface;

at least one planar return path formed in the same surface as the plurality of spiral grooves for connecting the inlet space of one spiral groove with the outlet space of another spiral groove; and at least one entry point positioned on the second surface to thread fluid flow tubing into at least one inlet space.

2. The tube support of claim 1, wherein said at least one radial slot is formed by aligned openings in wall structures forming said grooves.

3. A disk shaped tube support for use in countercurrent chromatography apparatus, comprising:

an upper surface and a lower surface; and a tube support pattern formed in the upper surface and configured to accommodate at least one layer of fluid flow tubing, wherein the tube support pattern comprises at least one spiral groove having an inlet space and an outlet space formed on the upper surface and at least one planar return path formed on the same surface as the at least one spiral groove for connecting the inlet space with the outlet space.

4. The tube support of claim 3, wherein the pattern comprises a single spiral groove and a single return path.

5. The tube support of claim 3, wherein the pattern comprises a single spiral groove and a plurality of return paths.

6. The tube support of claim 3, wherein the tube support pattern comprises a plurality of spiral grooves and a plurality of planar return paths.

7. The tube support of claim 6, wherein the plurality of spiral grooves are interleaved.

8. The tube support of claim 3, wherein the tube support pattern comprises at least two spiral grooves of different spiral pitch.

* * * * *